United States Patent [19]

Stokes et al.

[11] Patent Number: 5,282,844
[45] Date of Patent: Feb. 1, 1994

[54] HIGH IMPEDANCE, LOW POLARIZATION, LOW THRESHOLD MINIATURE STERIOD ELUTING PACING LEAD ELECTRODES

[75] Inventors: Kenneth B. Stokes, Minneapolis, Minn.; Fred Lindemans, Lt Limbricht, Netherlands

[73] Assignee: Medtronic, Inc., Minneapolis, Minn.

[21] Appl. No.: 887,560

[22] Filed: May 18, 1992

Related U.S. Application Data

[63] Continuation of Ser. No. 759,191, Sep. 10, 1991, abandoned, which is a continuation of Ser. No. 539,102, Jun. 15, 1990, abandoned.

[51] Int. Cl.$^5$ .............................................. A61N 1/05
[52] U.S. Cl. ...................................... 607/120; 607/121
[58] Field of Search ............... 128/784, 785, 786, 642, 128/419 P

[56] References Cited

U.S. PATENT DOCUMENTS

| | | | |
|---|---|---|---|
| 3,476,116 | 11/1969 | Parsonnet et al. | 128/417 PG |
| 4,502,492 | 3/1985 | Bornzin | 128/785 PG |
| 4,506,680 | 3/1985 | Stokes | 128/786 PG |
| 4,711,251 | 12/1987 | Stokes | 128/784 PG |
| 4,934,381 | 6/1980 | MacGregor | 128/784 PG |
| 4,953,564 | 9/1990 | Berthelsen | 128/784 PG |

OTHER PUBLICATIONS

Article by Seymour Furman, entitled: "Decreasing Electrode Size and Increasing Efficiency of Cardiac Stimulation", *Journal of Surgical Research*, vol. 11, No. 3, (Mar. 1971), pp. 105-110.
Article by Werner Irnich, entitled: "Considerations in Electrode Design for Permanent Pacing", *Cardiac Pacing: Proceedings of the Fourth International Symposium of Cardiac Pacing* (H. J. Thalen, Ed.) 1973, pp. 268-274.
Article by Fred W. Lindemans and Adriaen N. E. Zimmerman, entitled: "Acute Voltage, Charge, and Energy Thresholds as Functions of Electrode Size for Electrical Stimulation of the Canine Heart" *Cardiovascular Research*, vol. 13, No. 7, pp. 383-391 (Jul. 1979).
Article by Fred Heinemann, Richard Schallhorn and John Helland, entitled: "Clinical Performance of Steroid Eluting and Microporous Platinized Electrodes", 1 page. (date unknown).
Article by Richard Scallgorn and Kimberly Oleson, entitled: "Multi-Center Clinical Experience with an Improved Steroid-Eluting Pacemaker Lead", 1 page (date unknown).
Medtronic Product Brochure, entitled: "CAPSURE®SP Steroid-Eluting Endocardial Leads, Technical Manual", 10 pages (cover and pp. 1-9), (Sep. 1990).

*Primary Examiner*—William E. Kamm
*Assistant Examiner*—Scott M. Getzow
*Attorney, Agent, or Firm*—Reed A. Duthler; Harold R. Patton

[57] ABSTRACT

A small diameter, unipolar or bipolar, atrial or ventricular transvenous or epimyocardial pacing lead with a porous, platinized, steroid eluting cathode electrode exhibiting an effective surface area in the range of 0.1 to 4.0 mm$^2$, preferably 0.6 to 3.0 mm$^2$, provides low stimulation thresholds in the range of 0.5 volts, 0.5 milliseconds, very high pacing impedance (800 to 2,000 Ω), relatively low polarization, good to excellent sensing, and adequately low source impedance. The high pacing impedance prolongs the longevity of pacing pulse generators and allows for the miniaturization of their components. The low thresholds allow large safety factors at low applied voltages, which also contribute to increased battery longevity.

24 Claims, 4 Drawing Sheets

HIGH IMPEDANCE, LOW POLARIZATION, LOW THRESHOLD MINIATURE STERIOD ELUTING PACING LEAD ELECTRODES

This is a continuation of copending application(s) Ser. No. 07/759,191 filed on 10 Sep. 1991, which is also a continuation of application Ser. No. 07/539/102 filed on Jun. 15, 1990. now abandoned.

BACKGROUND OF THE INVENTION

1. Field of the Invention

This invention relates generally to chronically implanted medical electrode leads and, in particular, to cardiac pacing leads with an electrode structure which minimizes chronic pacing thresholds and drain on the pacing pulse generator power source.

2. Description of the Prior Art

The safety, efficacy and longevity of an implanted pacemaker system depends (in part) on the performance of its pacing lead(s), the electronic circuits of the pacemaker pulse generator, the integrity of the pulse generator and the capacity and reliability of the pulse generator power source. These inter-related components of the pacemaker system optimally are matched in a fashion that accommodates ever increasing demands on the modes of operation and function of the system in conjunction with an overall reduction in its size, an increase in its longevity and an increased expectation in the reliability of the entire system. During the past thirty years, the technology of cardiac pacing has significantly advanced, with implantable pacemakers displaying an ever increasing variety of pacing modalities, substantially broadening the indications for pacemaker use. In conjunction with this advancement, there has been extensive research and development effort expended to optimize the performance of pacing leads and their reliability.

In the past ten years, substantial improvements in reliable stable chronic pacemaker stimulation and sensing thresholds have been achieved which in turn have allowed the development of smaller and longer-lived pacemakers that can be used with those leads with excellent safety margins and reliability. As new circuits are developed with lower "overhead" current drains, however, and as the circuits increase in complexity to allow for ever increasing pacemaker capabilities in their programmable functions, modes and memory, the longevity of the device depends increasingly more on the characteristics of the lead. In addition, implanters prefer that pacing lead bodies be made ever thinner, to occupy less space in the venous system, without diminishing or detracting from the mechanical strength and integrity of the lead body.

In the early days of cardiac pacing, very high geometric surface area electrodes were employed with bulky and short-lived pacemaker pulse generators. Early investigators including Dr. Victor Parsonnet advanced designs of pacing electrodes for achievement of low polarization and low thresholds while presenting a relatively small effective surface area for the delivery of a stimulating impulse in designs known as differential current density (DCD) of the type shown in U.S. Pat. No. 3,476,116. The DCD electrode (like all pacing electrodes of that time) suffered excessive chronic tissue inflammation and instability and was not pursued commercially.

Subsequent researchers, including Dr. Werner Irnich explored in considerable detail the electrode-tissue interface and sought to arrive at an optimum exposed electrode surface area for both stimulation thresholds and sensing. Dr. Irnich in "Considerations in Electrode Design For Permanent Pacing" published in *Cardiac Pacing; Proceedings of the Fourth International Symposium of Cardiac Pacing* (H. J. Thalen, Ed.) 1973, pages 268–274, argued that the field strength (E) required to stimulate varies as $E = v_r [1/r + d]^2$ where v equals applied voltage (threshold, v), r equals electrode radius and d equals fibrous capsule thickness. He further argues that the mean value for d equals about 0.7 mm, regardless of electrode radius. Therefore, the smaller the electrode radius the lower threshold (assuming E is a constant) until r equals d. When $r < d$, thresholds rise again. Dr. Irnich had concluded that the exposed hemispherical electrode at the tip of the lead should have a radius in the order of 0.7 to 1.0 mm which would result in an exposed surface area of 3–6 mm$^2$. However, Dr. Irnich went on in his article to propose a somewhat different design employing wire hooks designed to penetrate the myocardium to hold the electrode in position. These active fixation wire hook electrodes never achieved popularity and were supplanted by passive fixation tined and active fixation screw-in endocardial pacing leads.

In a later paper, "Acute Voltage, Charge and Energy Thresholds as Functions of Electrode Size for Electrical Stimulation of the Canine Heart", by F. W. Lindemans and A. N. E. Zimmerman; *Cardiovascular Research. Vol. XIII. No.* 7, pp. 383–391, Jul., 1979, the author demonstrates that an electrode radius of about 0.5 mm is optimal in the acute situation. However, it was recognized that the benefits of a small electrode surface area would be lost when the fibrous capsule gets thicker than about 0.5 mm (as Irnich also states), and for that reason (and others stated in the article), electrodes of such small surface area could not be used chronically.

Dr. Seymour Furman had also studied the relationship of electrode size and efficiency of cardiac stimulation and presented a ball-tip/exposed spaced coil electrode and a small hemispheric electrode in his article entitled "Decreasing Electrode Size and Increasing Efficiency of Cardiac Stimulation" in *Journal of Surgical Research*, Volume 11 Number 3, Mar., 1971, pages 105–110. Dr. Furman concluded that the practical lower limit of electrode surface area was in the range of 8 mm$^2$ observing that impedance increased as an inverse function of the surface area.

Electrodes of many shapes including cylindrical, ball-tip, corkscrew, ring tip and open cage or "bird cage" configurations were pursued with exposed electrode surface areas tending toward 8 mm$^2$ in the mid 1970's.

More recently, various investigators have emphasized materials and their relationship to the considerations involved in optimizing electrode design. For example, the Medtronic U.S. Pat. No. 4,502,492 discloses a low polarization, low threshold electrode design of the early to mid 1980's which was commercialized as the "Target Tip ®" pacing leads in numerous models including Models 4011, 4012, 4511 and 4512. The tip electrode of the Target Tip ® leads was generally hemispherical and provided with circular grooves. The electrode was fabricated of platinum, coated over its external surface with a plating of platinum black. The combination of the relatively low electrode surface area and platinum black contributed to state-of-the-art thresholds in that time period. Other manufacturers marketed porous platinum mesh (Cardiac Pacemakers, Inc.), totally porous sintered (Cordis Corporation), glassy and vitreous carbons (Siemens), and laser drilled metal (Telectronics Ppty. Ltd.) electrodes in that same time period.

A considerable breakthrough in the development of low threshold electrode technology occurred with the invention of the steroid eluting porous pacing electrode of Stokes U.S. Pat. No. 4,506,680 and related Medtronic U.S. Pat. Nos. 4,577,642, 4,606,118 and 4,711,281, all incorporated herein by reference. The electrode disclosed in the '680 patent was constructed of porous, sintered platinum or titanium, although carbon and ceramic compositions were mentioned. Within the electrode, a plug of silicone rubber impregnated with the sodium salt of dexamethasone phosphate or the water soluble forms of other glucocorticosteroids was placed in a chamber. The silicone rubber plug allowed the release of the steroid through the interstitial gaps in the porous sintered metal electrode to reach the electrode-tissue interface and prevent or reduce inflammation, irritability and subsequent excess fibrosis of the tissue adjacent to the electrode itself. The porous steroid eluting electrodes presented a source impedance substantially lower compared to similarly sized solid electrodes and presented significantly lower peak and chronic pacing thresholds than similarly sized solid or porous electrodes. Those two advantages of steroid eluting electrodes allowed the use of relatively small surface area electrodes of about 5.5 mm$^2$ (CAPSURE® SP Model 5023, 5523 leads sold by Medtronic, Inc.) to raise the pacing impedance without sacrificing the ability to sense heart activity. The smaller electrode size permitted by the '680 patent invention resulted in higher current density during stimulation pulses, provided more efficient stimulation of the heart tissue with lower current drain from the implanted pacemaker power source. In addition, the localized nature of the drug treatment minimized the systemic assimilation of the drug and avoided undesirable side effects for the patient.

The 8 mm$^2$ surface area CAPSURE® steroid eluting lead Models 4003, 4503, 4004, and 4504 sold by Medtronic, Inc. have enjoyed remarkable commercial success to the present time. However, many physicians are not taking full advantage of properties of the electrode to save battery current and, therefore, longevity attainable by programming pacemaker pulse voltage to a safety margin level above the thresholds afforded by these leads. The quest to provide even lower stimulation thresholds and improved sensing and otherwise increase the performance and reliability of the pacing leads continues. One objective is to achieve markedly lower stimulation thresholds and to convince the physicians to accept and program lower voltage stimulation pacing pulses.

The impedance of the lead as a whole is a function of the resistance of the lead conductor and the electrode tip as well as the effective impedance of the electrode-tissue interface. An inefficient way or means to raise impedance is to increase the resistance of the conductors. This wastes current as heat. It is preferable to decrease lead current drain with more efficient control of the electrode-tissue interface impedance. This can be done by reducing the geometric surface area of the cathode. However, it is commonly believed that small electrodes are inefficient at sensing natural depolarizations of the cardiac tissue. This is not necessarily true, however. The amplitude of the intrinsic cardiac depolarization signals (typically the ventricular QRS and/or atrial P-wave complexes) is essentially independent of electrode size, as measured on a high, megohm range input impedance oscilloscope. The problem is that the sense amplifiers of modern pulse generators have comparatively lower input impedance—typically about 35 k$\Omega$. The impedance of the QRS or P-wave signal (or "source impedance") increases as the electrode surface area decreases. Thus, a 5 mm$^2$ polished electrode will produce QRS or P-waves with about 5 k$\Omega$ source impedance. According to Kirchof's law, the attenuation of the signal in the generator's amplifier is $1/(1+Zin/Zs)$ where Zin is the input impedance of the amplifier and Zs is the source impedance of the signal to be sensed. Thus, a 5 k$\Omega$ signal into a 35 k$\Omega$ amplifier will have its amplitude reduced by $1/(1+35/5)=12.5\%$. In marginal cases, this may make the difference between being able to sense properly or not being able to sense. Therefore, it is important to keep the source impedance low, preferable to attenuate less than 5% of the cardiac signal, that is, $Zs<1800\ \Omega$, for a 35 k$\Omega$ amplifier.

Thus, there is a trade-off with geometric surface area of the cathode electrode between the demands for low current drain and adequate sensing. In addition, it is desirable to achieve relatively low polarization effects so that they do not distort the electrogram of evoked or intrinsic cardiac depolarizations or leave a postpulse potential of sufficient magnitude to be mistakenly sensed as a QRS or P-wave by the amplifier.

SUMMARY OF THE INVENTION

It is thus an object of the present invention to reduce the effective surface area of pacing electrodes to a point well below the presently accepted dimensions to increase pacing impedance without increasing thresholds and without negatively impacting sensing capabilities.

The present invention provides a body-implantable lead for the delivery of an electric stimulus to a desired body site, particularly the atrial or ventricular chambers of a patient's heart. This lead presents a very high (greater or equal to 800 ohm) pacing impedance with low peak and chronic thresholds, low source impedance and excellent sensing in a size of approximately 1.5 mm$^2$ exposed geometric (or macroscopic) surface area.

Specifically, the lead of the present invention possesses an electrode with an exposed geometric surface area in the range of 0.1–4.0 mm$^2$, preferably between 0.6 and 3.0 mm$^2$, with about 1.0 mm$^2$ providing optimum performance. The lead has a pacing impedance of 1400±260 ohms, a source impedance of about 1650±410 ohms in both chambers of the heart. The lead of the present invention constitutes a pacing lead having a spherical, hemispheric or disk shaped exposed distal tip electrode of approximately 1 millimeter in diameter fabricated of platinized porous platinum (or other porous electrode material), loaded with glucocorticosteroid. In at least one embodiment, the electrode is attached to the distal end of a pacing lead of about 1.0 mm or 3 to 4 French in overall diameter.

Both endocardial and epicardial leads may be fabricated in accordance with the teachings of the present invention.

In another aspect of the present invention, DCD electrode technology may be successfully employed with a steroid eluting release device and with apertures in the range of 0.1 to 4.0 mm$^2$.

BRIEF DESCRIPTION OF THE DRAWINGS

These and other objects and advantages of the present invention may be fully understood and appreciated in conjunction with the attached drawings and the following detailed description of the preferred embodiments where the same numerals are employed to denote the same or similar features throughout.

DETAILED DESCRIPTION OF THE DRAWINGS

Before describing the specific features of the preferred embodiments of the present invention certain matters should be defined. First of all, the practice of the present invention contemplates the employment of a steroid or other drug with an electrode possessing a mechanism for allowing the drug to be eluted through and/or around the electrode in order to reach the endocardial or myocardial cells in the vicinity of the tip of the pacing lead in order to reduce, if not eliminate entirely, the acute and chronic inflammation occasioned by the cellular foreign body and physical irritation response to the tip of the lead. As described in the aforementioned Stokes' patents, the electrode is preferably fabricated of body compatible electrically conducting material with or without specific steroid eluting passages but generally with a porous structure either throughout the body of the electrode or at its surface. The porosity of the electrode surface or body provides a large surface area for sensing whereas the overall dimension or shape of the exposed electrode defines a comparatively smaller surface area for stimulation. The porous structure thus presents a microscopic (or "fractal") large surface area for sensing and a macroscopic or geometrically measured very small surface area for stimulation. Acceptable electrode materials and the associated fabrication techniques employed to achieve the micro-porous structure, as well as the porosity of that structure are all set forth in the aforementioned prior art patents and in the Richter et al U.S. Pat. No. 4,773, 433, the Heil et al U.S. Pat. No 4,819,661, the Thoren et al U.S. Pat. No. 4,149,542, the Robblee U.S. Pat. No. 4,677,989, the Heil et al U.S. Pat. No. 4,819,662, the Mund et al U.S. Pat. No. 4,603,704, the Skalsky et al U.S. Pat. No. 4,784,161, and the Szilagyi U.S. Pat. No. 4,784,160 and other patents and literature in the prior art.

Furthermore, the present invention may be practiced in the context of electrode structures that have heretofore been referred to as conventional exposed electrodes and the DCD electrode structures of the type shown in the aforementioned Parsonnet patent. In this regard, it will be observed in the following description of the preferred embodiments that electrodes of the present invention may be fabricating having characteristics of both the conventional and the DCD electrode structures. Dr. Parsonnet, in his early work on the DCD electrode, sought to reduce the polarization overvoltage (shown in FIG. 2 of his '116 patent) and the resulting postpulse polarization voltages which made and still make it difficult to distinguish the heart's P-waves or R-waves from those postpulse polarization voltages within 5 to 100 milliseconds after the delivery of the stimulus. In the practice of the present invention, the electrodes may be internalized in the DCD manner or externalized in the conventional manner. In the DCD context, the macroscopic surface area through which current is emitted during stimulation is defined by the aperture area presented to the cells in the vicinity of the tip of the pacing lead. The large, microscopic surface area is effected, as shown in FIG. 4 of the Parsonnet '116 patent, by the conductor coil within the distal portion of the lead body. In the present invention, the conductor coil may be rendered textured or porous by one or more of the aforementioned techniques, and steroid is eluted as described further herein below.

Figure 1:
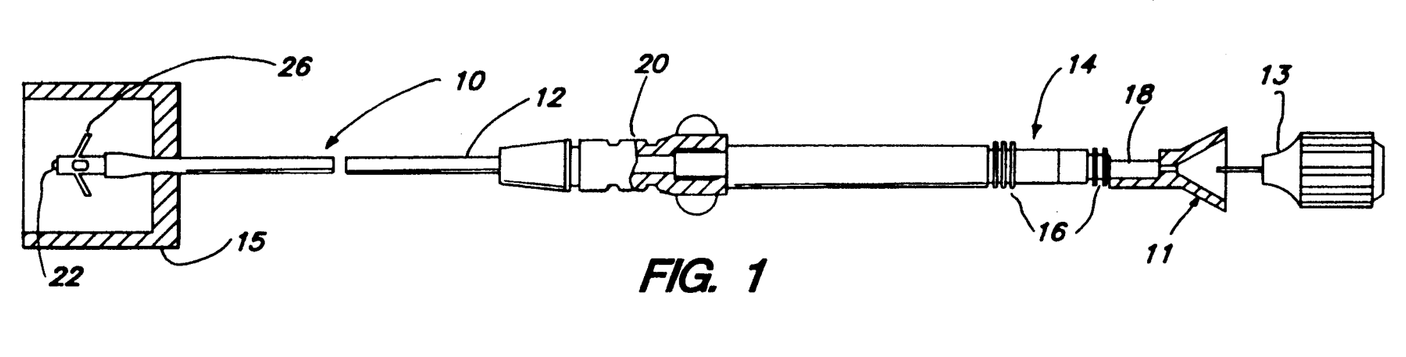
FIG. 1 shows a side plan view of an endocardial, unipolar, ball-tip electrode pacing lead according to the present invention.

FIG. 1 illustrates a plan view of an exposed electrode constructed in accordance with the present invention. The lead includes an elongated lead body 10 covered by an insulative sleeve 12. Insulative sleeve 12 may be fabricated of any flexible biocompatible and biostable insulator especially silicone rubber or polyurethane. At the proximal end of the lead, terminal assembly 14 is adapted to couple the lead to an implantable pacemaker pulse generator. Terminal assembly 14 is provided with sealing rings 16 and a terminal pin 18, all of a type known in the art. An anchoring sleeve 20 (shown partially in cross-section) slides over lead body 10 and serves as a point for suturing the lead body to body tissue at the insertion point of the lead into the vein or tissue in a fashion known in the art. Anchoring sleeve 20 and terminal assembly 14 may be conveniently fabricated of silicone rubber.

The lead shown in FIG. 1 further includes a stylet guide 11 and stylet assembly 13 coupled to the terminal pin 18 for imparting stiffness to the lead during the insertion and placement of the lead transvenously into either the right ventricle or the right atrium of the heart.

The stylet guide and stylet assembly are discarded after use and before connection of the terminal pin 18 to a pacemaker pulse generator.

At the distal end of the lead 10, a tine protector 15 is shown (in cross-section) protecting the tines until the lead is used. Tines 26 are employed to passively retain the tip electrode 22 in position against the endocardium as is well known in the pacing art.

The lead assembly 10 of FIG. 1 includes a multifiler conductor coil extending from the terminal pin 18 to the tip electrode 22. FIG. 1 depicts a unipolar lead and it should be understood that the present invention may be implemented in a bipolar lead design employing a second conductor extending from a second exposed cylindrical terminal surface area near the proximal end of the lead to an exposed ring electrode spaced $\geq 8$ mm from the distal tip electrode 22 as is well known in the art. The $\geq 8$ mm spacing is necessary because the current sense amplifier bandpass center frequency is about 25-30 Hz. Closer spacings are possible if the sense amplifier bandpass center frequency is shifted to higher values accordingly, and if higher gains are used.

Figure 2:
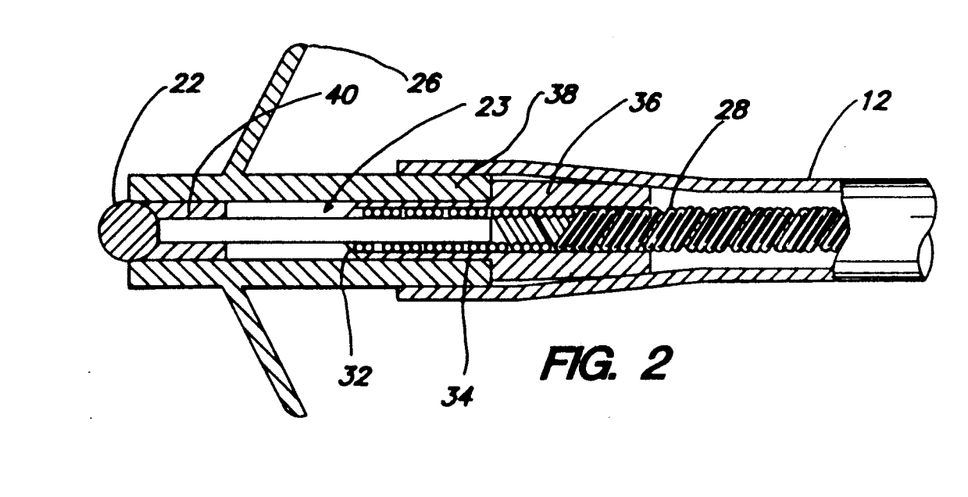
FIG. 2 shows a cross-sectional view of the ball-tip electrode of the lead shown in FIG. 1.

Referring now to FIG. 2, it shows in cross section a view of the distal lead portion of the preferred embodiment of the electrode of the present invention and its connection to the lead conductor 28. In FIG. 2, the distal electrode 22 is depicted as a porous platinum ball covered with platinum black at the end of a metal pin 23 of platinum extending from the tip electrode 22 to the distal end of the conductor coil 28. The conductor coil 28 is attached to the proximal end of the pin by crimping at point 34 of crimping member 36 at the time of manufacture. Silicone adhesive may be used at point 32 to seal the assembly against leakage of blood into the conductor coil. The insulative sheath 12 is shown placed over the crimping member as well as the tine assembly 38 which is fit between the distal end of the insulative sheath 12 and the crimping member 54. A steroid-silicone rubber compound ring 40 is located proximal from the electrode ball.

Figure 3:
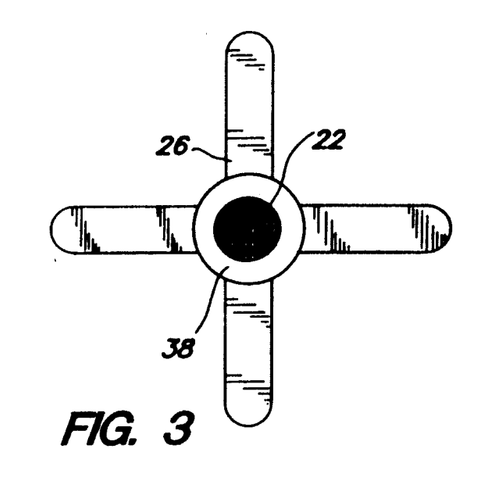
FIG. 3 shows an end plan view of the distal tip of the electrode of the lead shown in FIG. 1.

Referring now to FIG. 3, the end view of the ball-tip electrode 22, tines 26 and tine assembly 38 is shown. The ball-tip distal electrode 22 is constructed as shown in FIGS. 2 and 3 to present a circular, hemispheric or spherical exposed macroscopic surface area in the range between 0.1 and 4.0 square $mm^2$. The ball-tip electrode 22 is fabricated of porous, sintered platinum having a porosity in the range of 0.5 to 100 microns, employing "splat" powder in the sintering process.

The porous platinum electrode is electroplated with platinum black and the porosity, together with the platinum black coating is intended to reduce source impedance and polarization. The silicone backing sleeve 40 forms a monolithic controlled release device (MCRD), as it is loaded with an anti-inflammatory agent, e.g., a steroid dexamethasone sodium phosphate. The steroid also is deposited within the pores of the porous platinum electrode 22 by application of a solution of 200 mg U.S.P. dexamethasone sodium phosphate dissolved in 5.0 cc isopropanol and 5.0 cc distilled or deionized water as described in the aforementioned Stokes' patents. The MCRD weight and composition as well as the electrode surface area are critical to the electrode's overall performance. The small geometric macroscopic electrode size is intended to produce very high pacing impedance. The porous surface configuration together with platinum black electroplating and steroid contribute to a microscopically large surface area for low polarization, low source impedance and low thresholds. The porous surface also facilitates the retention of steroid and adhesion of the platinum black to the electrode surface.

Figure 4:
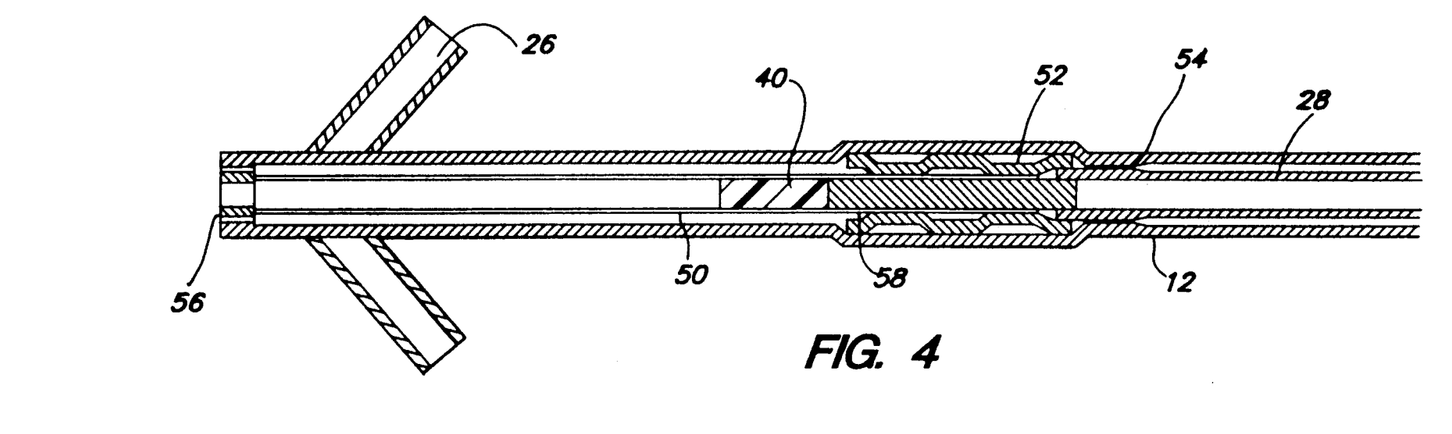
FIG. 4 shows a cross-sectional view of the distal portion of an endocardial, unipolar, DCD electrode pacing lead, according to the present invention.
Figure 5:
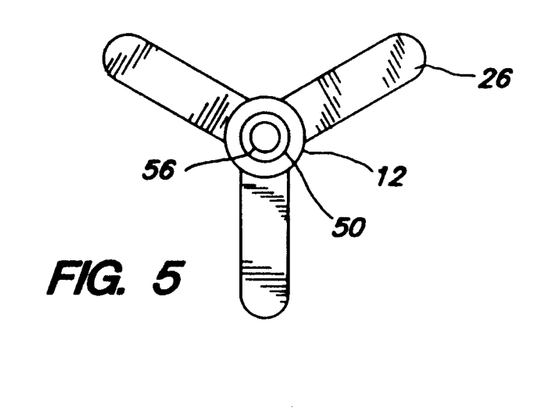
FIG. 5 shows an end plan view of the distal tip of the DCD electrode of the lead shown in FIG. 4.

Referring now to FIGS. 4 and 5, they depict a DCD electrode fabricated in accordance with the teachings of the present invention. A platinized coil 50 of platinum wire is crimped to conductor coil 28 using crimp sleeve 52 and crimp core 58. Silicone rubber adhesive 54 may be used to provide a seal to assure that blood does not leak into the conductor coil. The polymeric insulation tubing 12 extends to the end or just beyond the end of platinized coil 50. Three or four symmetrically placed tines 26 are placed close to the distal orifice or aperture 56. The aperture 56 of the tubing 12 presents a circular hole of 0.1 to 4.0 $mm^2$, about 0.62 $mm^2$ as shown. The lumen of the platinized coil is filled with a solution of 200 mg dexamethasone sodium phosphate in 5 cc water and 5 cc isopropanol. The solvents are allowed to evaporate, leaving a coating of steroid on the coils. The steroid loaded MCRD 40 is located at the proximal end of the platinized coil. The exposed surface of the platinized coil 50 must be large enough, preferably $\geq 50$ $mm^2$, to produce low polarization.

Past DCD electrodes required that the distal lumen be filled with conductive saline prior to insertion into the vein. This is not required with the steroid loaded lead, because the steroid acts as a wetting agent, allowing blood to fill the lumen as the lead is pushed down the vein.

In operation, charge transfer from electronic to ionic conduction occurs at the interface of the platinized coil and the blood or fibrotic tissue that eventually fills the lumen. Because this surface is large, polarization losses are low. Electric current is conducted through the blood and fibrotic tissue to the heart muscle to provide stimulation. Because the aperture 56 is small, acute thresholds are low and pacing impedance is high. The steroid controls inflammation in the surrounding tissue and helps to prevent or reduce chronic threshold rise.

Figures 6, 7, 8, 9, 10:
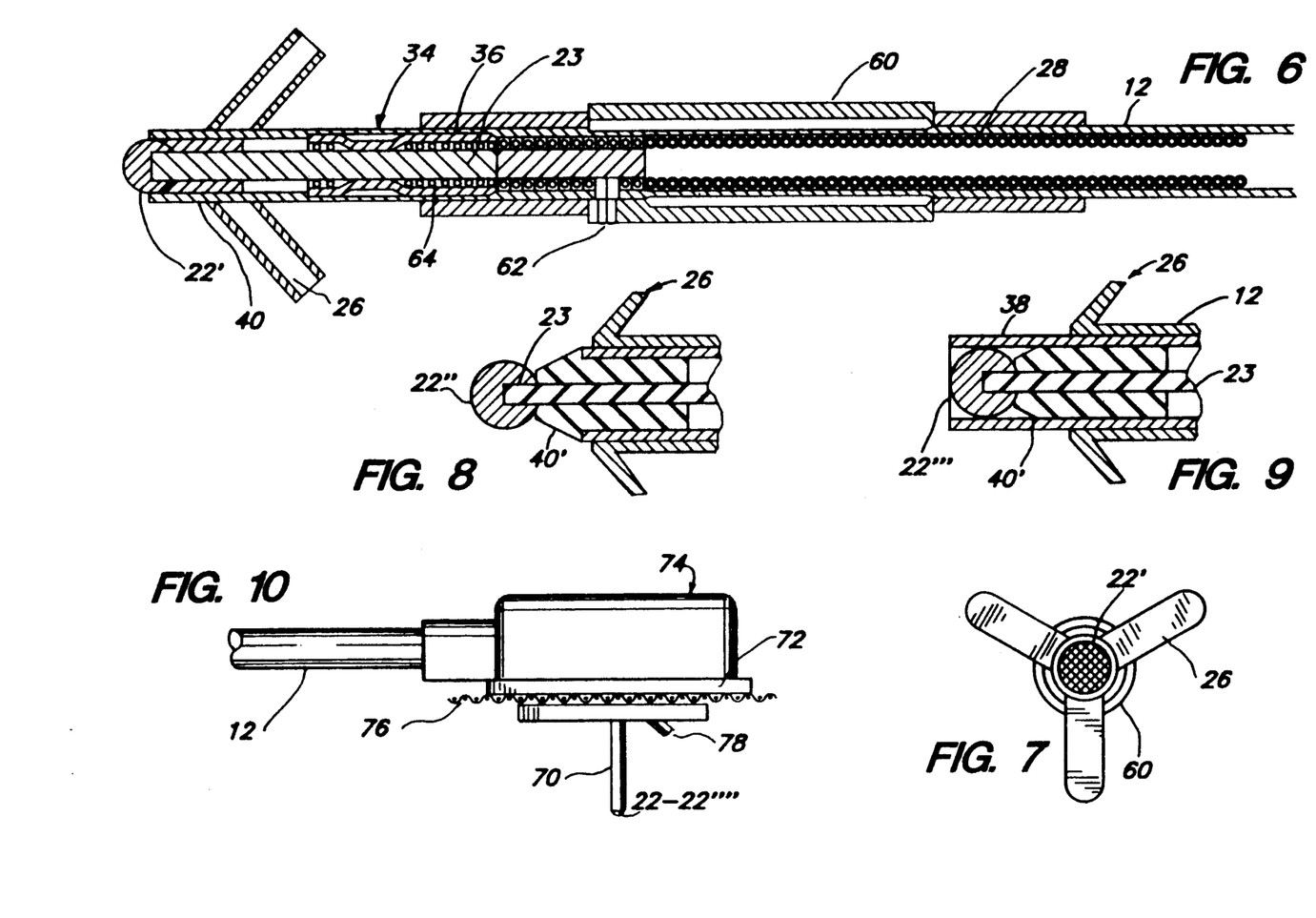
FIG. 6 shows a cross-sectional view of the distal tip portion of a further endocardial, bipolar, cylindrical tip electrode pacing lead according to the present invention.
FIG. 7 shows an end plan view of the distal tip electrode of the lead shown in FIG. 6.
FIG. 8 shows a cross-sectional view of the distal tip portion of a further embodiment of the ball-tip electrode according to the present invention.
FIG. 9 shows a cross-sectional view of the distal electrode of a modified DCD electrode according to the present invention.
FIG. 10 shows a plan view of the distal portion of a bipolar epicardial pacing lead according to the present invention.

Referring now to FIGS. 6 and 7, they depict an alternative design of the bipolar, endocardial pacing lead of the present invention, and in particular, a modified electrode assembly of the present invention. The lead of FIG. 6 is constructed in similar fashion to the lead of FIGS. 1-3 and, to the extent possible, the same numerals will be employed to describe the same or equivalent elements of these two embodiments of the lead. The principal differences between FIGS. 1-3 and FIGS. 6 and 7 are that the lead of FIGS. 6 and 7 is bipolar, possessing a ring electrode 60 spaced from tip electrode 22', the tine elements 26 are constructed somewhat differently and the quadrafiler conductor coil 28 comprises two pair of bifiler, commonly wound, separately insulated conductors, each respectively connected to one of the two electrodes. Thus, at point 62, two of the conductor wires are attached to the ring electrode 60, and at point 64 the remaining two conductor wires contact the pin 23 and crimp sleeve 36 which is crimped against the coils 64 at point 34. The pin 23 extends through the steroid impregnated ring 40.

The tip electrode 22' is fabricated of the same materials and treated in the same fashion as the tip electrode 22 of the embodiment of FIGS. 1-3. FIGS. 6 and 7 thus illustrate a bipolar embodiment of the pacing lead of the present invention.

Turning now to FIG. 8, it discloses a further ball-tip electrode 22" attached to a pin 23 extending back to a similar connection with a coiled wire conductor (not illustrated). The tip electrode 22″ is virtually fully exposed as is a portion of the distal end of the steroid eluting MCRD 40′. Thus the electrode depicted in FIG. 8 illustrates an extreme example of the exposed "nanotip" concept of the present invention and may be employed in either endocardial or epi/myocardial lead designs where the tip electrode may penetrate myocardial tissue. The exposed surface of the MCRD ′ thus allows for steroid elution in a path in both through and around the spherically shaped electrode 22″.

Turning now to FIG. 9, it depicts a still further embodiment of the distal portion of the electrode of the present invention. The electrode of FIG. 9 is a modification of the electrode depicted in FIGS. 1 to 3 except that, unlike the electrode depicted in FIG. 8, the ball-tip electrode 22‴ is fully retracted within the distal portion of the tine bearing member 38. The inside diameter of the lead tip, that is the inside diameter of the tine element 38, is preferably 0.040 inches which equals a 0.8 mm² orifice. Only a hemispheric portion of the surface of the ball electrode 22‴ is exposed in this embodiment of the invention.

The aforementioned embodiments of the present invention are all illustrated as endocardial pacing leads wherein the electrode or lead tip may or may not be designed to pass through the endocardium and into the myocardium of the heart. In substitution for the tined fixation mechanisms shown, any of the endocardial lead embodiments may be provided with active screw-in fixation mechanisms.

Figure 11:
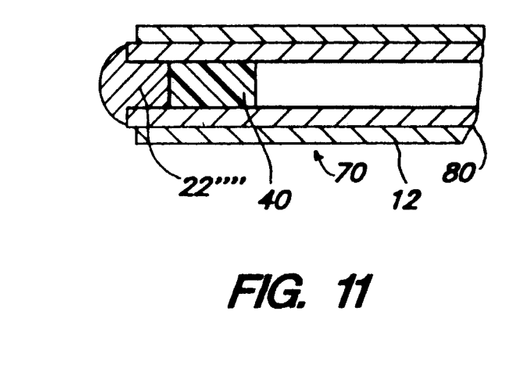
FIG. 11 shows a cross-sectional view of the distal tip portion of the electrode, preferably employed in the epicardial electrode of FIG. 10.

FIGS. 10 and 11 depict a further embodiment wherein the concept of the present invention is embodied in a bipolar epicardial pacing lead wherein the tip electrode 22⁗ is mounted on a stem 70 extending from a platform 72 of an epicardial lead body 74 to penetrate into the myocardium. While not specifically shown, the epicardial lead of FIG. 10 may be affixed in place by fixation hooks or screws (partially shown at 78) or sutures. The specific configuration of the electrode 22⁗ may take the form of any of the electrodes 22–22‴- previously described with the exception that the outer surface or tubular member of the extension 70 may need to be stiff enough to allow the tip electrode to penetrate the epicardial membrane. It will be understood, furthermore, that the epicardial version of the lead of the present invention may further incorporate a DCD design within body 74 or 70 of the type shown, for example, in the aforementioned Parsonnet '116 patent.

However, preferably the tip electrode 22⁗ and stem 70 are constructed as shown in FIG. 11. The stem 70 preferably comprises a hollow metal tube 80 having an MCRD 40 located at any point therein between the tip electrode 22⁗ and the point where the tube is mechanically and electrically connected to the conductor coil (not shown) within housing 74. The tip electrode 22⁗ is attached to the tip of tube 80, and the exterior of the tube 80 is insulated by outer tube 12. The steroid in the MCRD 40 elutes through the porous tip electrode 22⁗.

The bipolar mesh electrode 76 shown in FIG. 10 may also be soaked with steroid in same fashion as tip electrode 22⁗. The epicardial lead may also be constructed in unipolar fashion substituting a porous fabric for metallic mesh electrode 76 to allow fixation to the epicardium by fibrotic tissue ingrowth. Said unipolar leads may also be fixed to the heart by sutures, obviating the need for the fabric mesh. Such leads may otherwise possess the features of Medtronic U.S. Pat. No. 4,010,758 and designs discussed in a paper by K. Stokes, "Preliminary Studies on a New Steroid Eluting L Epicardial Electrode", *PACE, Vol.* 11., pp. 1797–1803, Nov., 1988, incorporated herein by reference.

The electrodes of each of the foregoing embodiments may be fabricated by coating machined electrode blanks or by dipping the end of pin 23 (of FIGS. 1–3 and 6–10) into a binder, then dipping it into a fluidized bed of platinum splat powder, which adheres to the pin 23 in a generally ball shape, and then sintering the powder. The electrode of FIG. 11 may be constructed by applying a mixture of the binder and splat powder to the opening of the tube 80 and then sintering it in situ.

The previously described embodiments of the present invention are illustrative of the construction and features of the very small diameter tip electrodes and pacing leads of the present invention. As previously indicated, the prior art had progressed to the point where the lower limit for effective macroscopic surface areas was believed to be within the range between 5.5 mm² and 8 mm². Studies that we have conducted with steroid free, small macroscopic surface area porous electrodes in both the exposed and DCD configuration confirmed the expectation and findings of the aforementioned prior investigators in the field.

Figure 12:
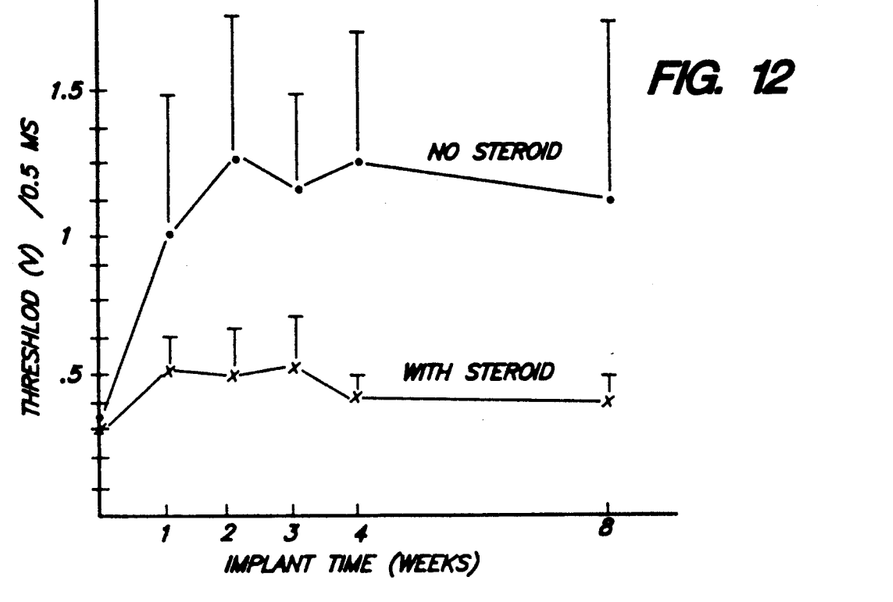
FIG. 12 depicts graphically the performance of the exposed electrodes of the present invention with steroid elution against electrodes of the same size and configuration without steroid elution; and, FIG. 13 depicts graphically the performance of a DCD electrode of the present invention with steroid elution against a test DCD electrode of the same size and configuration without steroid elution.

In regard to exposed electrodes of the present invention with steroid compared to those electrodes without steroid, the difference in stimulation thresholds is striking. FIG. 12 depicts the results of a paired study in canines of the ventricular "nanotip" leads with and without steroid over an 8 week study period. The stimulation thresholds show a marked rise for the leads without steroid as compared to those leads with steroid.

The actual data from the paired "nanotip" ventricular canine study is set forth in Tables I and II as follows:

TABLE I

PAIRED VENTRICULAR DATA

| Implant Time (Weeks) | N | 0.5 ms Threshold (v) | | 0.5 ms Pacing Impedance (Ω) | |
|---|---|---|---|---|---|
| | | No Steroid | With Steroid | No Steroid | With Steroid |
| 0 | 4 | 0.32 ± .05 | 0.30 ± .08 | 1300 ± 200 | 1300 ± 300 |
| 1 | 4 | 1.0 ± .53 | 0.52 ± .09 | 870 ± 140 | 950 ± 170 |
| 2 | 4 | 1.3 ± .51 | 0.52 ± .15 | 780 ± 320 | 880 ± 520 |
| 3 | 3 | 1.2 ± .35 | 0.57 ± .15 | 1000 ± 210 | 1100 ± 180 |
| 4 | 2 | 1.3 ± .56 | 0.45 ± .07 | 970 ± 200 | 1160 ± 330 |
| 8 | 2 | 1.2 ± .64 | 0.45 ± .07 | 1200 ± 430 | 990 ± 48 |

TABLE II

PAIRED VENTRICULAR DATA

| Implant Time (Weeks) | N | R-Wave Amplitude (mV) (Slew Rate) (v/s) | | R-Wave Source Imped. (Ω) | |
|---|---|---|---|---|---|
| | | No Steroid | With Steroid | No Steroid | With Steroid |
| 0 | 4 | 38 ± 3.9 (≧8.4 ± 1.9) | 29 ± 7.6 (≧6.7 ± 4.2) | 1400 ± 330 | 1450 ± 510 |
| 1 | 4 | 26 ± 4.9 | 29 ± 5.7 | 1100 ± 190 | 975 ± 171 |

TABLE II-continued

| | | PAIRED VENTRICULAR DATA | | | |
|---|---|---|---|---|---|
| | | R-Wave Amplitude (mV) (Slew Rate) (v/s) | | R-Wave Source Imped. (Ω) | |
| Implant Time (Weeks) | N | No Steroid | With Steroid | No Steroid | With Steroid |
| 2 | 3 | (4.1 ± .16) 25 ± 5.7 | (4.1 ± 2.2) 27 ± 2.2 | 1100 ± 290 | 1200 ± 270 |
| 3 | 3 | (4.1 ± .77) 26 ± 6.9 | (4.3 ± 1.5) 28 ± 2.9 | 1000 ± 200 | 1300 ± 210 |
| 4 | 2 | (4.2 ± .38) 25 ± 9.9 | (5.0 ± 1.8) 28 ± 2.8 | 1150 ± 210 | 1350 ± 490 |
| 8 | 2 | (4.1 ± .85) 27 ± 4.2 (4.9 ± .28) | (5.7 ± 0) 31 ± 1.4 (≧8.4 ± 2.3) | 1200 ± 430 | 1000 ± 0 |

Figure 13:
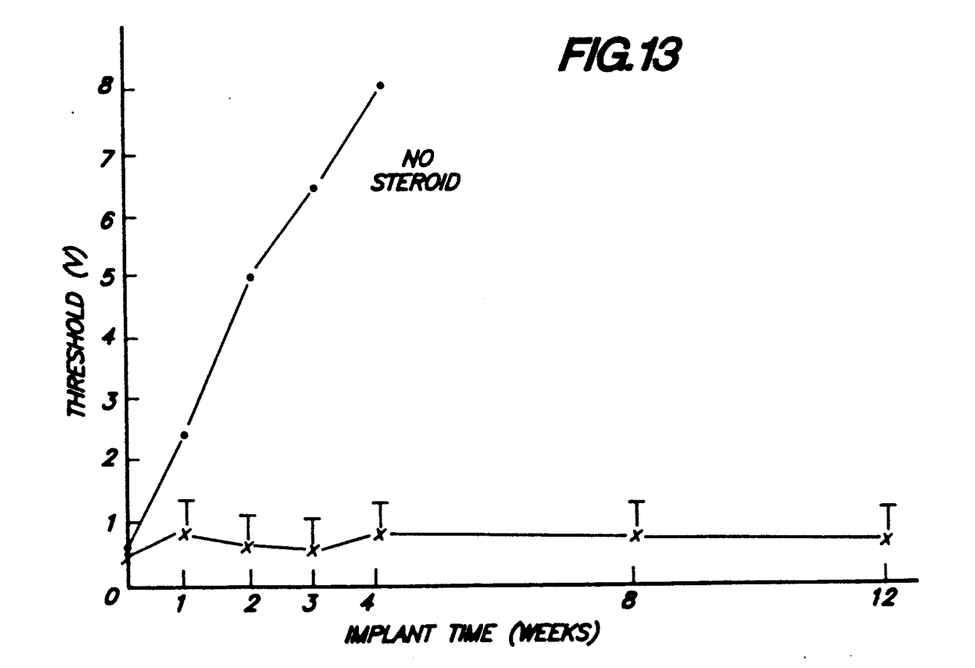

In our studies without steroid, the DCD electrodes having apertures of 0.1 to 0.2 mm$^2$, and probably up to 0.5 mm$^2$ do not work. They go to exit block and stay there. A DCD electrode having a 0.6 mm$^2$ aperture without steroid exhibits a threshold rise of from 0.5 volts to over 8 volts in three weeks as exhibited in the graph of FIG. 13. However, with steroid, the same size DCD electrode exhibits a chronic threshold rise of from 0.5 volts to approximately 0.8 volts over a 12 week implant time as shown in the lower curve of FIG. 13.

In regard to the performance of the DCD electrodes the data from the studies conducted in dogs are presented in the following Tables III and IV.

TABLE III 0.6 mm$^2$ APERTURE STEROID ELUTING DCD ELECTRODE AS A FUNCTION OF IMPLANT TIME IN CANINES
(N = 5)

| Implant Time (Weeks) | 0.5 ms Threshold (v) | Pacing Impedance (Ω) | R/P-Wave Amplitude (mV) | R/P-Wave Source Impedance (s) | Slew Rate (v/s) |
|---|---|---|---|---|---|
| VENTRICLE | | | | | |
| 0 | 0.45 ± .23 | 1300 ± 570 | 29 ± 5.9 | 2250 ± 790 | 5.4 ± 1.2 |
| 1 | 0.85 ± .50 | 1000 ± 320 | 25 ± 2.9 | 1400 ± 500 | 4.0 ± .83 |
| 2 | 0.7 ± .48 | 1000 ± 670 | 28 ± 1.9 | 1300 ± 860 | 4.5 ± 1/7 |
| 3 | 0.67 ± .38 | 1000 ± 610 | 29 ± 3.8 | 1300 ± 740 | 4.4 ± 1.8 |
| 4 | 0.87 ± .62 | 1300 ± 617 | 28 ± 3.9 | 1200 ± 680 | 5.5 ± 2.6 |
| 8* | 0.82 ± .57 | 990 ± 580 | 28 ± 3.6 | 1100 ± 670 | 4.4 ± 2.7 |
| 12* | 0.82 ± .57 | 1200 ± 380 | 28 ± 4.2 | 1300 ± 420 | 4.6 ± 2.7 |
| ATRIUM | | | | | |
| 0 | .34 ± .08 | 2900 ± 220 | 13 ± 3.6 | 3100 ± 580 | 4.4 ± 1.9 |
| 1 | 1.2 ± .69 | 1400 ± 210 | 6.2 ± 2.0 | 1700 ± 210 | 1.4 ± 1.2 |
| 2 | 1.1 ± .62 | 1600 ± 190 | 7.6 ± 2.4 | 2100 ± 280 | 1.9 ± 1.5 |
| 3 | 0.7 ± .33 | 1700 ± 100 | 9.0 ± 3.9 | 2200 ± 420 | 2.2 ± 1.5 |
| 4 | 0.84 ± .45 | 1700 ± 110 | 8.2 ± 2.7 | 1900 ± 250 | 1.8 ± 1.3 |
| 8 | 0.28 ± .08 | 1600 ± 210 | 8.5 ± 3.4 | 1800 ± 270 | 2.6 ± 1.8 |
| 12* | 0.47 ± .09 | 1600 ± 240 | 8.5 ± 3.3 | 1700 ± 0 | 2.5 ± 1.9 |

*N = 4

TABLE IV

| | | PAIRED DCD THRESHOLDS AND PACING IMPEDANCES | | | |
|---|---|---|---|---|---|
| | | Exposed Electrode | 0.5 ms Thresholds (v) | | Pacing Impedance (Ω) |
| Implant Time (Weeks) | N | Area (mm$^2$) | No Steroid | With Steroid | No Steroid | With Steroid |
| 0 | 1 | 0.15 | 0.8 | 2.1 | 19000 | 30000 |
| 0 | 2 | 0.62 | 0.5 ±.3 | 0.6 ±.07 | 3300 ±350 | 4300 ±2500 |
| 1 | 1 | 0.15 | 6.9 | >10 | 17000 | 39000 |
| 1 | 1 | 0.62 | 2.4 | 1.2 | 3400 | 4000 |
| 2 | 1 | 0.15 | 6.1 | 7.8 | 15000 | 26000 |
| 2 | 1 | 0.62 | 5.0 | 1.4 | 3300 | 3500 |
| 3 | 1 | 0.15 | >10 | 3.8 | — | 38000 |
| 3 | 1 | 0.62 | 6.5 | 2.2 | 3800 | 4400 |
| 4 | 1 | 0.15 | 9.6 | 3.3 | 16000 | 33000 |
| 4 | 1 | 0.62 | 8.1 | 1.7 | 5400 | 3400 |

In regard to the myocardial electrodes of the type shown particularly in FIGS. 10 and 11, animal implant data of 1.5 mm$^2$ macroscopic surface area electrodes with and without steroid is presented in the following Tables V and VI.

TABLE V

MYOCARDIAL 1.5 mm$^2$ ELECTRODES
CANINE VENTRICULAR STIMULATION

| Implant Time (Weeks) | 0.5 ms Thresholds | | 0.5 ms Pacing Impedance ($\Omega$) | |
|---|---|---|---|---|
| | With Steroid (N = 4) | No Steroid (N = 3) | With Steroid (N = 4) | No Steroid (N = 3) |
| 0 | 0.50 ± .10 | 0.35 ± .10 | 4400 ± 4500 | 3800 ± 2100 |
| 1 | 0.86 ± .40* | 1.4 ± .40 | 1400 ± 350 | 1300 ± 180 |
| 2 | 0.50 ± .11 | 1.9 ± .28 | 1600 ± 210 | 1600 ± 300 |
| 3 | 0.45 ± .12 | 1.1 ± .55 | 1600 ± 150* | 2150 ± 1200 |
| 4 | 0.47 ± .22 | 0.83 ± .32 | 1600 ± 210 | 1300 ± 550 |
| 8 | 0.45 ± .12 | 0.63 ± .12 | 1400 ± 160 | 1300 ± 430 |
| 12 | 0.47 ± .17 | 0.70 ± .10 | 1200 ± 270 | 1500 ± 260** |

*N = 3
**N = 2

TABLE VI

MYOCARDIAL 1.5 mm$^2$ ELECTRODES
CANINE VENTRICULAR SENSING

| Implant Time (Weeks) | R-Wave | | | |
|---|---|---|---|---|
| | Amplitudes (mv) | | Source Impedance ($\Omega$) | |
| | With Steroid (N = 4) | No Steroid (N = 3) | With Steroid (N = 4) | No Steroid (N = 3) |
| 0 | 17 ± 4.3 | 23 ± 13 | 3900 ± 1200 | 7600 ± 1500 |
| 1 | 17 ± 5.7 | 19 ± 1.0 | 2400 ± 460 | 3400 ± 510 |
| 2 | 17 ± 7.8 | 20 ± 3.6 | 2500 ± 450 | 3600 ± 1500 |
| 3 | 18 ± 7.9 | 23 ± 5.0 | 2600 ± 330 | 2900 ± 590 |
| 4 | 18 ± 8.0 | 22 ± 4.7 | 2400 ± 220 | 3000 ± 600 |
| 8 | 24 ± 7.1 | 23 ± 5.3 | 1900 ± 96 | 2300 ± 610 |
| 12 | 19 ± 8.3 | 24 ± 5.9 | 1800 ± 220 | 2400 ± 870 |

Thus it can be seen that the very small "nanotip", exposed and DCD electrodes of the present invention satisfy the aforementioned desirable characteristics of a pacing lead, that has low stimulation thresholds very high pacing impedance (800-2500 ohms) relatively low polarization, good to excellent sensing, and adequately low source impedance. The high pacing impedance prolongs the longevity of pacing pulse generators and allows for the miniaturization of their components. The low thresholds allow large safety factors at low applied voltages, which also contribute to increased battery longevity.

While the embodiments of the present invention have been described in particular application to cardiac pacing, it will be understood that the invention may be practiced in other electrode technologies where the aforementioned characteristics are desirable, including neurological and muscle stimulation applications. Moreover, the miniaturization of the electrodes afforded by the present invention may advantageously allow the clustering of two or more electrode structures at the tip of a stimulation/sensing lead or probe. While not specifically illustrated above, the present invention may advantageously be implemented in tip electrode configurations of the type illustrated in Sleutz et al U.S Pat. No. 4,662,382 in order to provide practical closely spaced bipolar stimulation and sensing.

The invention has been described in detail with particular reference to the preferred embodiments thereof, but it will be understood that variations and modifications can be effected within the scope of the following claims.

What we claim is:

1. A body implantable lead for stimulation and sensing of a desired body tissue site, comprising:

a. an electrical conductor having a proximal end and a distal end;
    b. insulating sheath means for covering said conductor between said proximal and distal ends thereof;
    c. electrical connector means coupled to said proximal end of said conductor for electrically connecting said lead to a pulse generator;
    d. electrode means electrically coupled to said distal end of said electrical conductor for conducting electrical energy to and from said body tissue site desired to be stimulated and sensed, said electrode means having an exposed macroscopic surface area of less than 3.0 mm$^2$ exposed to body fluids and tissue;
    e. wherein said electrode means comprises a body of a porous metallic or other conductive material with high microscopic surface area in proportion to said exposed macroscopic surface area, mounted to a distal end of a conductive pin and extending radially from said conductive pin, a proximal end of said pin being coupled to said distal end of said electrical conductor; and
    f. drug dispensing means mounted around said pin, proximal to said porous body, for storing a drug to be dispensed while allowing dispensing of said drug, through said porous body, to counter undesirable interactions between said lead and said body site.

2. A lead according to claim 1, wherein said electrode means is formed of porous metallic or other conductive materials from the class of materials consisting essentially of platinum, palladium, titanium, tantalum, rhodium, iridium, carbon, vitreous carbon, and alloys, oxides and nitrites of such metals or other conductive materials.

3. A lead according to claim 1, wherein said drug dispensing means comprises a fluid permeable polymer body located within said insulating sheath means, said polymer body containing a water soluble form of said drug.

4. A lead according to claim 1, wherein said drug is a water soluble form of an anti-inflammatory drug.

5. A lead according to claim 4, wherein said drug is a glucocorticosteroid.

6. A lead according to claim 4, wherein said drug is the sodium salt of dexamethasone phosphate.

7. A lead according to claim 1, wherein said exposed macroscopic surface area is in the range of between 0.10 and 2.0 mm$^2$.

8. A lead according to claim 1, wherein said exposed macroscopic surface area is generally hemispherical in shape.

9. A lead according to claim 1, wherein:
said drug dispensing means is situated in a position in relation to said porous electrode portion to provide for the delivery of said drug only through said porous body to said body tissue site.

10. A lead for body implantation within a patient for stimulation and sensing of a desired cardiac tissue site, said lead having an electrode of differential current density type, comprising:
   a. an electrical conductor having a proximal end and a distal end;
   b. electrical connector means coupled to the proximal end of said conductor for electrically connecting said lead to a cardiac pulse generator;
   c. electrode means coupled to said distal end of said conductor for conducting electrical energy to and from said cardiac tissue site;
   d. insulating sheath means for covering and electrically insulating said electrical conductor from body fluids and tissue extending between said electrode means and said electrical connector means;
   e. insulating body means coupled of the distal end of said insulating sheath means, said insulating body means having a wall spaced apart from and extending around said electrode means to prevent said electrode means from directly contacting said tissue site and thereby defining an electrode chamber, said wall further including an aperture provided therein for allowing body fluid ingress within said chamber and to said electrode means;
   f. wherein said electrode chamber aperture is in the range of 0.1 to 3.0 mm$^2$ in area; and
   g. drug dispensing means carried adjacent the insulating body means for storing a drug to be dispensed while allowing dispensing of said drug within said chamber when wetted by the ingress of body fluids, such that said drug elutes through said chamber aperture, thereby countering undesirable interactions between said lead and said body site.

11. A lead according to claim 10, wherein said drug dispensing means comprises a fluid permeable polymer body located with said insulating body means and adjacent said electrode means, said polymer body containing a water soluble form of said drug.

12. A lead according to claim 10, wherein said drug is a water soluble form of an anti-inflammatory drug.

13. A lead according to claim 12, wherein said rug is a glucocorticosteroid.

14. A lead according to claim 12, wherein said drug is the sodium salt of dexamethasone phosphate.

15. A lead according to claim 10, wherein said electrode means comprises a length of electrically conductive wire coupled at one end to said distal end of said electrical conductor.

16. A lead according to claim 15, wherein said conductive wire is provided with a coating of metallic black.

17. A lead according to claim 15, wherein an exposed surface of said conductive wire is formed of porous platinum.

18. A lead according to claim 10, wherein said electrode means comprises an exposed surface area of within said insulating body means of greater than 50 mm$^2$.

19. A body implantable lead, comprising:
   a. an electrical conductor having a proximal end and a distal end;
   b. insulating sheath means for covering said conductor between said proximal and distal ends thereof;
   c. electrical connector means coupled to said proximal end of said conductor for electrically connecting said lead to a pulse generator;
   d. electrode means electrically coupled to said distal end of said electrical conductor for conducting electrical energy to and from said body tissue site desired to be stimulated and sensed, said electrode means comprising a body of a porous metallic or other conductive material with high microscopic surface area in proportion to macroscopic surface area, mounted to a distal end of a conductive pin and extending radially from said conductive pin, a proximal end of said pin being coupled to said distal end of said electrical conductor; and
   e. drug dispensing means mounted around said pin, proximal to said porous body, within said insulating sheath, for storing a drug to be dispensed while allowing dispensing of said drug through said porous body to counter undesirable interactions between said lead and said body site.

20. A lead according to claim 19, wherein said porous body is generally circular in cross section.

21. A lead according to claim 20, wherein said porous body is generally spherical.

22. A lead according to claim 19 wherein said porous body extends radially between said conductive pin and said insulating sheath.

23. A lead according to claim 19 wherein said drug dispensing means extends distal to said insulating sheath.

24. A lead according to claim 19 wherein said porous body is located within said insulating sheath.

* * * * *